(12) United States Patent
Heidlas et al.

(10) Patent No.: US 6,599,533 B1
(45) Date of Patent: Jul. 29, 2003

(54) HOMOGENOUS WATER-FREE FORMULATIONS CONTAINING GLYCEROPHOSPHOLIPIDS AND POLAR OR LIPOPHILIC SUBSTANCES, METHOD FOR THE PRODUCTION THEREOF

(75) Inventors: Jürgen Heidlas, Trostberg (DE); Karl-Heinz Zirzow, Trostberg (DE); Johann Wiesmüller, Garching (DE); Jürgen Graefe, Trostberg (DE)

(73) Assignee: Degussa AG, Trostberg (DE)

( * ) Notice: Subject to any disclaimer, the term of this patent is extended or adjusted under 35 U.S.C. 154(b) by 0 days.

(21) Appl. No.: 09/381,530

(22) PCT Filed: Mar. 26, 1998

(86) PCT No.: PCT/EP98/01789

§ 371 (c)(1),
(2), (4) Date: Sep. 21, 1999

(87) PCT Pub. No.: WO98/43674

PCT Pub. Date: Oct. 8, 1998

(30) Foreign Application Priority Data

Mar. 27, 1997 (DE) ......................... 197 13 093
Mar. 27, 1997 (DE) ......................... 197 13 094

(51) Int. Cl.⁷ ............................ A61K 9/14; A23D 7/00
(52) U.S. Cl. ..................... 424/489; 424/450; 424/401; 426/613; 426/615
(58) Field of Search ...................... 424/450, 401, 424/489; 426/613, 615

(56) References Cited

U.S. PATENT DOCUMENTS

| | | | |
|---|---|---|---|
| 4,363,826 A | 12/1982 | Fukuda et al. | |
| 4,681,617 A | 7/1987 | Ghyczy et al. | |
| 4,871,768 A | 10/1989 | Bistrain et al. | |
| 4,973,483 A | 11/1990 | Michel et al. | |
| 5,101,840 A | 4/1992 | Riehl, Jr. | |
| 5,321,145 A | 6/1994 | Schafer | |
| 5,362,504 A | 11/1994 | Kamper et al. | |
| 5,525,746 A * | 6/1996 | Franke .................. | 554/12 |
| 5,597,602 A * | 1/1997 | Peter et al. ............. | 426/478 |
| 5,643,601 A | 7/1997 | Gross et al. | |
| 5,770,559 A * | 6/1998 | Manning et al. ......... | 514/2 |
| 5,837,221 A * | 11/1998 | Bernstein et al. ........ | 424/9.52 |

FOREIGN PATENT DOCUMENTS

| | | |
|---|---|---|
| DE | 4006563 | 9/1991 |
| DE | 4407933 | 9/1994 |
| DE | 4403989 | 8/1995 |
| EP | 0051833 | 5/1982 |
| EP | 0556392 | 8/1993 |
| EP | 0659755 | 6/1995 |
| FR | 2717043 | 9/1995 |
| WO | 9611669 | 4/1996 |

OTHER PUBLICATIONS

Derwent Publications Ltd., Patent Abstract of Japan No. 62 116516A—Nov. 18, '85.

Heidlas J.E. "Propane Extraction in Food processing" — Food Marketing and Technology, vol. 8, No. 6, Dec. 1994, pp. 38–40.

* cited by examiner

Primary Examiner—Russell Travers
Assistant Examiner—Shahnam Sharareh
(74) Attorney, Agent, or Firm—Fulbright & Jaworski L.L.P.

(57) ABSTRACT

This invention relates to homogeneous, anhydrous formulations which contain glycerophospholipids and polar or lipophilic substances (eg, physiologically active ingredients) in a molar ratio of 1:0.001 to 1:2, and maybe anhydrous formulation aids, eg, in the form of glycerol, in a molar ratio of 1:0.001 to 1:1, expressed in terms of the glycerophospholipids, the components forming such stable aggregates with one another as to render the formulations ideal for the preparation of dispersions, emulsions and/or suspensions in many fields of application, these including the food-processing sector, biotechnology, and the pharmaceuticals industry. The formulations are produced in an extraction column using compressed hydrocarbons, and are obtained from the column as a melt.

14 Claims, No Drawings

HOMOGENOUS WATER-FREE FORMULATIONS CONTAINING GLYCEROPHOSPHOLIPIDS AND POLAR OR LIPOPHILIC SUBSTANCES, METHOD FOR THE PRODUCTION THEREOF

This application is a 371 of PCT/EP98/01789 filed on Mar. 26, 1998 which claims foreign priority to German Applications 19713093.3 filed on Mar. 27, 1997 and 19713094.1 filed Mar. 27, 1997.

The subject of this invention are homogeneous formulations containing glycerophospholipids and polar or lipophilic substances, and a method of producing a these formulations.

Glycerophospholipids play an important physiological role as building blocks for membranes, especially during compartmentation in biological systems. They are accordingly ubiquitous in animal, plant and microbial forms of life.

Chemically speaking, natural glycerophospholipids consist of glycerol which is esterified in the $C_1$ and $C_2$ positions with fatty acids and carries a phosphatide ester in the $C_3$ position. From the point of view of quantity, by far the most important natural glycerophospholipids are the phosphatidyl derivatives phosphatidyl choline, phosphatidyl serine, phosphatidyl ethanolamine, phosphatidyl inositol and phosphatidic acid. In certain cell systems, however, there are, in addition, high concentrations of other phospholipids, eg, plasmalogens, cardiolipins or sphingomyelins.

In principle, it is possible to synthesise glycerophospholipids in vitro by means of chemical and/or enzymatic processes. The structure of the products obtained can correspond to that of natural glycerophospholipids, but can also be "synthetic". However, at the present time, biological sources still take precedence in industrial-scale production because they are readily available. This applies especially to plant lecithins, eg, from soybeans, rape or sunflower seed. These lecithins are obtained as a mixture of various phospholipid classes, so-called "raw lecithin", in the refining process during the production of cooking oils. The most important animal source of glycerophospholipids is the yolk from hens' eggs, which is characterized by a high phosphatidyl choline content. There are various methods available, eg, solvent extraction, with which it is possible to increase the proportion of certain glycerophospholipid classes in the naturally occurring mixtures, and/or, usually with the help of chromatographic separation methods, to obtain them in uniform form; here too, phosphatidyl choline is particularly important.

By means of chemical and/or enzymatic processes, eg, by means of hydrolysis, hydroxylation or hydrogenation, naturally occurring glycerophospholipids can be modified such that their surface-active properties, in particular, are changed.

The main reason why surface-active glycerophospholipids are used technologically is because of their emulsifying effect, which is exploited specifically to stabilise emulsions or suspensions, eg, traditionally in the food-processing sector, in industry, and in the pharmaceuticals sector. In addition, glycerophospholipids can also be used physiologically, because in vivo they fulfil important functions, especially as building blocks for membranes in biological cells. By virtue of this fact, and because they are toxically innocuous, natural glycerophospholipids in particular, especially phosphatidyl cholines and cephalins, are used for products or formulations which can be supplied directly or indirectly to humans. Of particular interest is their use in food and in pharmaceutical products. It is also known that the resorption, pharmacokinetics and/or the pharmacological effect of active ingredients used in drugs can be varied by formulating them with glycerophospholipids.

In the preparation of emulsions and dispersions, eg, in the formulation of pharmaceutical active ingredients, but also in other technical areas, it is often desirable for the active ingredients to be dispersed as finely and homogeneously as possible. This necessitates, eg, a small particle size. Formulations and methods of producing them with which the active ingredient can be more finely distributed by way of the formulation than was possible so far are accordingly of great interest and can be of far-reaching importance.

According to the prior art, there are three main methods of formulating glycerophospholipids with polar or lipophilic substances:

(1) formulation of the (dissolved) polar substances or (liquid or dissolved) lipophilic substances in membrane-forming glycerophospholipid vesicles or liposomes ("micellar system"), (2) formulation by means of incorporating fine (microcrystalline) particles of the solid polar or lipophilic substance in glycerophospholipids ("micro-crystalline system"), and (3) formulation by means of binding the polar or lipophilic substance chemically to glycerophospholipids (chemical-bond system).

In "micellar-system" formulations, the polar substances are dissolved in polar solvents, usually water, and are surrounded by a single- or multi-layer membrane, eg, a bilayer membrane, consisting of surface-active glycerophospholipids. The lipophilic substances, in liquid form or dissolved in suitable solvents, are encapusulated in a similar way. A recent survey on this formulation technique is contained in H. Hauser, Phospholipid Vesicles in Ceve. G. (ed.), Phospholipid Handbook, Marcel Dekker, New York, 1993, pp. 603–637. Building up a micellar bilayer membrane for the formulation of polar substances in water or of lipophilic substances is, however, not unproblematic, and certain esters of phosphoric acid, eg, in the form of glycerophospholipids such as phosphatidyl choline, may have to be present in the membranes in order to impart the required stability.

The inclusion rates for the active ingredients to be formulated are often low, so that large active-ingredient losses have to be allowed for during production of the formulation. In addition, sterol derivatives such as cholesterol are often needed to stabilise the membrane. Attempts have also been made to stabilise the membrane by forming an adduct—by means of a chemical bond—between cholesterol and the substance to be formulated (eg, J. L. Murtha et al., J. Pharm. Sci 83 (9), 1222–8, 1994). Another approach has been to produce liposomal formulations using supercritical carbon dioxide, rendering the use of large volumes of organic solvent unnecessary (Frederiksen L. et al, J. Pharmaceutical. Sci. 86, 921–8, 1997). Formulations of active ingredients, eg, through use of the liposome technique, have resulted in great progress, eg, in many therapies used in modern medicine; however, there are two main disadvantages, eg, in parenteral applications: for one, liposomes—as artificial micelles—have only a limited lifetime in vivo because lipid exchange reactions, in particular, can take place at membranes and thus destabilise the membranous vesicle or liposome, or even cause it to disintegrate, before it reaches the actual place of intended therapy. For another, especially in the case of larger micelles, the mononuclear phagocyte system becomes active, and leads to undesired immunological side reactions. For physical reasons, it is impossible to reduce the size of vesicular liposomes arbitrarily and thus to avoid the immune response, because the surface of the membrane, depending on its composition, will tear open as from a certain micelle size.

In formulations where polar or lipophilic substances are incorporated in micro-crystalline form in glycerophospholipids, the problem likewise arises that according to prior art, the size of the microcrystals cannot be arbitrarily reduced. If a solvent system is used, for example, in which both the polar/lipophilic substances and the glycerophospholipids are dissolved, and this solution is subjected, eg, to spray drying, the solubility limits of the substances and the glycerophospholipids are reached at different solvent concentrations during removal of the solvent, and a "microcrystalline formulation" is obtained. As the time needed to remove the solvent approaches zero, the size of the particles could, in theory, be reduced still further, but this is technically unfeasible.

The patent specification EP-B-O 493 578 describes the use of supercritical carbon dioxide to try and overcome these problems. For this process, however, both the emulsifier and the substance to be formulated must be soluble in supercritical carbon dioxide so that the requisite homogeneous distribution can be obtained. But the solubility of glycerophospholipids in supercritical carbon dioxide is only marginal, and only selected active ingredients can be used in this process. The first of these two disadvantages alone is sufficient to render the proposed method of formulating active ingredients with glycerophospholipids unsuitable.

Another method of producing a powdery drug form comprising one or more active ingredients and one or more carriers, which is conducted with the help of a fluid gas, is known from the EP-A-O 322 687. According to this method, a liquid medium containing the active-ingredient component and the carrier component is first of all brought into contact with the fluid gas; the liquid is then removed by the fluid gas, and an active ingredient/carrier preparation obtained which is free of liquid medium. By means of this process, in which, eg, $CO_2$, $N_2O$ and hydro-carbons in supercritical state can be used as fluid gases, and polymers, lipids, lecithins and waxes as carrier components, small hollow spheres are obtained in powder form by means of so-called spray-embedding. The liquid components contained in the formulation are separated completely from the preparation by means of a spray tower and one- or multi-component nozzles, and the preparation is obtained in powder form. The disadvantages of this "spray-embedding" process are, on the one hand, the technical complexity:

(i) The value-determining particle size of the solid formulation obtained is determined by a complicated nozzle design which is susceptible to technical problems;

(ii) Experience has shown that it is technically very difficult to remove extremely fine powder from the spray tower, because it is hardly practicable to collect the fine particles in a separator.

On the other hand, it is a disadvantage if all the liquid components (ie, also any liquid formulation aids that may be present) have to be completely removed, because the micro-crystalline powder obtained is only suitable for specific applications, eg, for the production of micro-encapsulations in polymers, with delayed drug release.

Formulations in which a substance of polar or lipophilic character is bound chemically to surface-active glycerophospholipids ("chemical-bond system"), of the type described, eg, by Hong et al. in Cancer Res. 50 (14), 4401–6 (1990), have the major disadvantage that this method is complicated and not generally applicable, an added problem being the fact that on account of the chemical bond, the substance's mode of action usually changes. Accordingly, this formulation strategy is limited in practice to just a few exceptional cases.

The general objective of an improved formulation, namely to obtain a molecularly disperse distribution between active ingredient and glycerophospholipid by means of molecular, preferably noncovalent interaction, is not achieved with the procedures described above.

Appropriate solutions to the problems outlined above are not known according to the prior art, and approaches to a solution have only been described for formulations of water-insoluble, non-polar substances (U.S. Pat. No. 4,973,465 or WO 91/16 068). It is thus of considerable interest to further improve active-ingredient distribution, especially in pharmaceutical formulations.

The object of this invention was thus to provide homogeneous, anhydrous formulations comprising active ingredients, carriers, and maybe formulation aids, which do not have the described disadvantages of hitherto known formulations and which, in particular, reduce or completely prevent the formation of micro-crystalline particles.

This objective was established by means of homogeneous, anhydrous formulations containing (A) one or more glycerophospholipids (B) one or more polar and/or lipophilic substances showing an affinity with glycerophospholipids (C) maybe one or more formulation aids with at least two hydroxyl groups, characterized in that the glycerophospholipid component (A) and the component (B) are present in a molar ratio of 1:0.001 to 2 and—in cases where (C) is present—the glycerophospholipid component (A) and the component (C) are present in a molar ratio of 1:0.001 to 1.

In this invention, glycerophospholipids are understood to be compounds containing a glycerol radical which is esterified with at least one fatty acid radical and with at least one phosphatide radical. Examples of suitable classes of glycerophospholipids include phosphatidic acids, phosphatidyl esters, lyso-phospholipids, cardiolipins and plasmalogens. Preference is given to phosphatidyl esters and lyso-phospholipids which are esterified with a fatty acid radical at the $C_1$ atom of the glycerol, and with a phosphatide radical at the $C_3$ atom of the glycerol. It is especially beneficial to select the glycerophospholipids (A) from compounds which have the general formula (I):

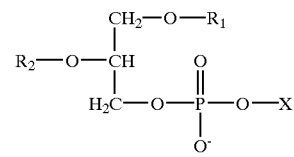

where $R_1$ and $R_2$ can be the same or different, and each stand for a fatty acid radical with the general formula (II):

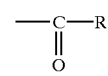

where R stands for straight-chain or branched-chain, saturated or mono- or polyunsaturated $C_6$ to $C_{24}$ fatty acid radicals, which may be substituted in the chain with, eg, OH or heteroatoms such as O, N or S, where $R_2$ can also be H, and where X is a radical from the series —H, $CH_2$—$CH_2$—

$NH_3^+$, $-CH_2-CH_2-N-(CH_3)_3^+$, $-CH_2-CH(NH_3^+)COO^-$, $-CH_2-CH(-OH)-CH_2-OH$ or

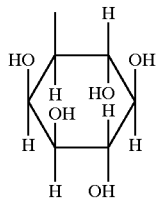

The average molecular weights of the glycerophospholipids can be used as a basis for calculating the molar ratios.

Surprisingly, it was found that when introduced into hydrophilic and/or lipophilic media and into two-phase systems, the formulations of the invention show a high level of stability and either do not dissociate into the starting components, or do so only to a minor extent. The formulations of the invention show solution behaviour which can be controlled selectively by way of the molar ratio of glycerophospholipid (A) to the polar or lipophilic substance (B): with an equimolar ratio of glycerophospholipid to polar substance, one possibility provided for according to the invention, the formulations are amphiphilic, ie, in a two-phase system they have a surface-active effect. If there is an excess of glycerophospholipid, these formulations are more lipophilic, ie, they can be incorporated well in oil. Water-soluble colouring agents, for example, which have been formulated with an excess of glycerophospholipid, form clear, coloured solutions in oil at temperatures >50° C. Through additional use of the formulation aid (C), the dispersibility and/or solubility in water, as well as the stability of the emulsion, can be decisively improved in all formulations of the invention. This is evident, for example, in formulation-aid-containing formulations of non-polar active ingredients, which, at temperatures >50° C., can be dispersed readily in water to form a stable emulsion; the formulation can be sterilised by means of a 0.2 μm filter without deaggregating. In the formulation of lipophilic substances, the solubility of the overall formulation in water is improved significantly.

Especially good properties in terms of the invention are shown by formulations which contain lecithins and/or cephalins as glycerophospholipid component (A).

As substances (B) with polar and/or lipophilic properties, it is preferable according to the invention to use physiological active ingredients or colouring agents, the molecular weight of which should be <1500 daltons, and, in particular, <500 daltons.

An essential aspect is that the substances (B) have an affinity with glycerophospholipids, this affinity not necessarily resulting in a covalent chemical reaction but—as is especially preferred in this case—being manifested in the formation of non-covalent interactions such as secondary valences, so-called hydrogen bonds, and/or lipophilic interactions. As this happens the system is stabilised, with formation of the homogeneous, anhydrous aggregates ("molecular self-assemblies") which are typical of the formulations of the invention and, as far as their structure is concerned, compare best with "solid solutions".

In this invention, physiological active ingredients are understood to be all compounds or classes of substances which have a regulating or controlling influence on metabolic processes. Especially when administered to mammals or humans, the effect is naturally dependent on the form in which the active ingredient is administered. The term "polar substance" or "lipophilic substance" accordingly covers all polar and also some water-soluble or lipophilic active ingredients in drugs which are suitable for topical and transdermal applications, or which can be administered through the mouth, parenterally or by way of inhalation and, in particular here, intravenously, intramuscularly, subcutaneously, intraperitoneally or intranasally.

The term also includes active ingredients used in cosmetics, and, in addition, agrochemicals such as fertilisers, plant growth regulators, herbicides and insecticides, and also biocides of general nature.

Of the large variety of physiological active ingredients in question, the water-soluble vitamins or fat-soluble vitamins, such as those of the groups A, D, E and K, are quoted by way of example. An example of the water-soluble colouring agents is Ponceau 4 R (E 124), while the carotinoids are important examples of the lipophilic colouring agents.

The formulations of the invention are anhydrous, ie, they preferably contain less than 5 wt. %, better still less than 3 wt. % and best of all less than 1 wt. % of water, expressed in terms of the overall weight of the formulation.

In addition, it is beneficial if the formulations of the invention are oil-free, preferably containing a maximum of 3 wt. % and, better still, a maximum of 2 wt. % of oil, ie, triglycerides, expressed in terms of the overall weight of the formulation. It is of particular advantage if the formulations of the invention are solid at room temperature, eg, in the form of a free-flowing powder.

According to the invention, the formulations may also contain one or more polyol compounds as formulations aids (C), the polyols pereferably being liquid polyols, especially $C_2-C_4$ compounds, and containing at least two hydroxyl groups. The greatest preference is given here to glycerol. The polyols in question can also be used in the form of arbitrary mixtures. It is of advantage, however, if the formulation aids for preparing the formulation are anhydrous, ie, preferably having a maximum water content of 5 wt. %, expressed in terms of the weight of the formulation aid.

In addition to the formulations, this invention includes a method of producing them, which is carried out in three main steps:

First of all, in step (a), substance (B) is provided in liquid form, eg, as a pure substance, assuming it is liquid under the conditions in question. It is preferable, however, if substance (B) is dissolved in an anhydrous solvent (mixture), ie, a solvent which preferably contains a maximum of 5 wt. % water. Polar and/or non-polar solvent (mixtures) are especially suitable for this purpose. It is also possible to admix the formulation aid (C), which again is anhydrous, with the solvent (mixture) in the molar ratios given. If a polar substance is to be formulated, this substance can also be dissolved exclusively in the anhydrous formulation aid.

The polar solvents provided for in the invention are solvents of protic and/or aprotic character. As protic solvents, primary monovalent $C_{1-10}$ alcohols, secondary monovalent $C_{3-10}$ alcohols and tertiary monovalent $C_{4-10}$ alcohols, as well as arbitrary mixtures thereof, have proved to be especially suitable. Preferred examples of aprotic solvents are halogenated $C_{1-10}$ hydrocarbons, especially chloroform, as well as ethers such as diethyl ether and tetrahydrofuran (THF), and also arbitrary mixtures thereof.

Suitable non-polar solvents are aliphatic or cyclic $C_{5-10}$ hydrocarbons, and/or triglycerides.

In special cases, it is useful in step (a) to use mixtures of polar and non-polar solvent (mixtures) in a weight ratio of max. 1:1.

The liquid or solution resulting from step (a) is then combined in step (b) with a glycerophospholipid (mixture)

(A) in such a way that the dissolved state of the components is maintained. The prerequisite for this is that the glycerophospholipid component (A) is also used in the dissolved state, for which purpose, once again, anhydrous polar—but also non-polar—solvents or mixtures thereof are especially suitable. In addition, a formulation aid (C) may be present.

Should it be necessary to use non-polar solvents in order to obtain a solution, aliphatic or cyclic $C_{5-10}$ hydrocarbons, preferably hexane and/or cyclohexane, and/or triglycerides, have proved suitable in steps (a) and/or (b), as was mentioned before. From the group of triglycerides, preference is given in the invention especially to natural vegetable oils.

The mixture of dissolved substances resulting from step (b) is subsequently subjected to an extraction process in order to remove the solvent (mixture). For the extraction, it is of advantage to use an extracting agent containing hydrocarbons such as propane and/or butane, which are gaseous under normal conditions. According to an especially preferred embodiment, the extraction is carried out in a rectifying column under a pressure between 1 and 50 MPa and at a temperature from 20 to 150° C., using an extracting agent containing propane and/or butane; the extraction is conducted in such a manner that the extraction mixture is distributed between a homogeneous lower phase comprising glycerophospholipid (mixture) (A), substance (B) and maybe formulation aid (C), and an upper phase containing the solvent and maybe the substance (B), and that the lower phase separates from the upper phase, with the formulation being obtained from the lower phase, which is generally in the form of a melt. The method of the invention for producing the formulation can thus be carried out with no significant loss of the substance to be formulated.

Under the conditions preferred according to the invention, the solution of starting materials obtained from steps (a) and (b) is extracted in a rectifying column by an extracting agent (mixture) coming from the bottom and preferably consisting of propane with up to 95 wt. % dimethyl ether (DME).

The extraction conditions preferred according to the invention are a pressure between 1 and 50 MPa and a temperature of 20 to 150° C., with pressures in the range between 3 and 20 MPa and temperatures of 30 to 100° C. having proved especially suitable. Following extraction, which is preferably conducted as a continuous, countercurrent process, the extracting agent (mixture) is conducted away, while the glycerophospholipid fraction, sinking in the form of a melt to the bottom of the column, takes up the substance (B) to be formulated, and also the formulation aid, if one was used; it is at this stage that the formulation containing the glycerophospholipid (mixture), the polar or lipophilic substance and, if one was used, the formulation aid, is actually formed, and this can take place entirely in the dissolved state. For improved separation of the starting mixture into a liquid upper phase and a lower phase (melt), it has proved highly beneficial to operate with a temperature gradient in the column, the temperature at the top being 5 to 50° C. higher than that at the bottom.

The fused formulation at the bottom of the column, which usually contains between 20 and 40 wt. % of extracting agent (mixture), can be discharged via a suitable arrangement of nozzles into an ambient-pressure environment and thus freed of extracting agent (mixture) by means of the resulting pressure reduction and/or an increase in temperature. The solvent (mixture) obtained as top product is likewise freed of extracting agent (mixture), again by means of a pressure reduction and/or an increase in temperature. For this purpose it is expedient to use a separator.

It is also possible to compress the extracting agent (mixture) and recycle it.

During production of the formulations of the invention in the manner described, it is especially beneficial if the fused glycerophospholipid (mixture) (A) can take up the substance (B), which is to be formulated, directly from the solvent (mixture) of the feed mixture. By virtue of the procedure of the invention and in contrast to hitherto known processes, no microcrystalline particles are formed. This explains why the claimed formulations are fully homogeneous.

Very generally, therefore, the method of the invention serves to transform substances of polar and/or lipophilic character into homogeneous formulations with lipophilic or amphiphilic properties, so that they can be used for applications which up till now were very difficult or completely impracticable.

This also explains why these homogeneous formulations, in keeping with the idea behind the invention, are especially suitable for the preparation of dispersions, emulsions and/or suspensions for the food processing industry, biotechnology, the agrochemicals, cosmetics and pharmaceuticals industries—here in particular for the formulation of active ingredients—but also for the paint and varnish industry and the leather industry.

Additional subject matter of the invention is a pharmaceutical preparation containing a formulation according to the invention, maybe together with carriers, aids, fillers and/or diluents such as are common in the pharmaceuticals industry.

Of particular interest here is the distribution in the claimed, stable formulations or aggregates with glycerophospholipids beneath the critical micelle concentration. These new possibilities are especially important for membrane-penetration processes.

The following examples illustrate a typical method of producing the formulations of the invention:

EXAMPLES

Example 1

Formulation of a Polar Substance Without a Formulation Aid, Using Two Solvents (ethanol and triglycerides)

5.1 g nicotinamide (polar substance) were dissolved completely in 84 g ethanol (99.8 %), added to 450 g of a mixture of 65 wt. % glycerophospholipids (natural mixture from soybeans) and 35 wt. % triglycerides (soybean oil), and mixed carefully by stirring at 45° C. The mixture obtained in this way was supplied by means of a high-pressure pump to an extraction column, approximately in the middle. The rectifying section of the column has about 5, and the stripping section about 7 theoretical stages. Compressed propane under a pressure of 60 bar served as extracting agent. At the feed stage of the column the temperature was about 75° C., at the top of the column 85° C. and at the bottom of the column 65° C. The ratio of the mixture supplied (feed) to the extracting agent (propane) was on average 5 wt. %. The empty-pipe speed of the extracting agent in the column was 2 mm/s.

The extracting agent conveyed out of the column head, loaded with oil and ethanol, was evaporated in a separator at approximately 70° C. and 8 bar, and thus freed of the oil and most of the ethanol. The oil-free formulation formed according to the method of the invention (oil content less than 2 wt. %) was discharged at the bottom of the extraction column into an ambient-pressure environment by way of an arrangement of nozzles. Due to spontaneous evaporation of the propane, the formulation cooled and a free-flowing powder was obtained. The proportion of nicotinamide in the homogeneous formulation was 1.7 wt. %, which corresponds to a molar ratio of 0.1 (calculated on the basis of an average molecular weight of 700 daltons for the glycerophospholipids).

Chemical analysis of the individual components of the formulation confirmed a constant composition during the extraction process.

Example 2

Formulation of a Polar Substance Using a Formulation Aid and Two Solvents 16 g nicotinamide (polar substance) were dissolved completely in a mixture of 30 g ethanol (99.8 %) and 21 g glycerol (anhydrous formulation aid) at 45° C., added to 500 g of a mixture of 65 wt. % glycerophospholipids (natural mixture from soybeans) and 35 wt. % triglycerides (soybean oil), and mixed carefully by stirring, likewise at 45° C. The mixture of dissolved substances was supplied by means of a high-pressure pump to an extraction column, approximately in the middle. The rectifying section of the column has about 5, and the stripping section about 7 theoretical stages. Compressed propane under a pressure of 50 bar served as extracting agent. At the feed stage of the column the temperature was about 70° C., at the top of the column 80° C. and at the bottom of the column 60 C. The ratio of the mixture supplied (feed) to the extracting agent (propane) was on average 3 wt. %. The empty-pipe speed of the extracting agent in the column was 2 mm/s.

The extracting agent conveyed out of the column head, loaded with oil and ethanol, was evaporated in a separator at approximately 70° C. and 8 bar, and thus freed of the oil and most of the ethanol. The oil-free formulation formed according to the method of the invention (oil content less than 2 wt. %) was discharged at the bottom of the extraction column into an ambient-pressure environment by way of an arrangement of nozzles. Due to spontaneous evaporation of the propane, the formulation cooled and a free-flowing powder was obtained. The proportion of nicotinamide in the formulation was 4.4 wt. %, which corresponds to a molar ratio of 0.28, expressed in terms of the glycerophospholipid; the proportion of 5.8 wt. % glycerol in the formulation corresponds to a molar ratio of 0.5, expressed in terms of the glycerophospholipid (calculated on the basis of an average molecular weight of 700 daltons for the glycerophospholipids).

Example 3

Formulation of a Polar Substance Using a Formulation Aid and One Solvent (triglycerides)

0.9 g nicotinamide (polar substance) were dissolved completely in 15 g glycerol (anhydrous formulation aid) at 45° C., added to 540 g of a mixture consisting of 60 wt. % glycerophospholipids (natural mixture from soybeans) and 40 wt. % triglycerides (soybean oil), and mixed carefully by stirring, likewise at 45 C. The mixture of dissolved substances was supplied by means of a high-pressure pump to an extraction column, approximately in the middle. The rectifying section of the column has about 5, and the stripping section about 7 theoretical stages. A compressed mixture of propane and about 25 wt. % butane under a pressure of 60 bar served as extracting agent. At the feed stage of the column the temperature was about 75° C., at the top of the column 85° C. and at the bottom of the column 65° C. The ratio of the mixture supplied (feed) to the extracting agent (propane/butane) was on average 5 wt. %. The empty-pipe speed of the extracting agent in the column was 2 mm/s.

The extracting agent mixture conveyed out of the column head, loaded with oil (but free of glycerol and nicotinamide), was evaporated in a separator at approximately 70° C. and 6 bar, and thus freed of the oil. The oil-free formulation formed according to the method of the invention (oil content less than 2 wt. %) was discharged at the bottom of the extraction column into an ambient-pressure environment by way of an arrangement of nozzles. Due to spontaneous evaporation of the extracting agent mixture, the formulation cooled and a free-flowing powder was obtained. The proportion of nicotinamide in the formulation was 0.3 wt. %, which corresponds to a molar ratio of 0.02, expressed in terms of the glycerophospholipid; the proportion of glycerol in the formulation was 4.4 wt. %, which corresponds to a molar ratio of 0.35, expressed in terms of the glycerophospholipid (calculated on the basis of an average molecular weight of 700 daltons for the glycerophospholipids).

Example 4

Formulation of a Lipophilic Substance Using Two Solvents (ethanol and triglycerides)

38 g DL-α-tocopherol (lipophilic substance) were added to 231 g of a dissolved mixture consisting of 56 wt. % glycerophospholipids (natural mixture from soybeans), 30 wt. % triglycerides (soybean oil), 5 wt. % anhydrous glycerol (formulation aid) and 9 wt. % ethanol (99.8 %) and mixed carefully by stirring at 45 C. The mixture of dissolved substances was supplied by means of a high-pressure pump to an extraction column, approximately in the middle. The rectifying section of the column has about 6, and the stripping section about 6 theoretical stages. Compressed propane under a pressure of 40 bar served as extracting agent. At the feed stage of the column the temperature was about 70° C., at the top of the column 75° C. and at the bottom of the column 65° C. The ratio of the mixture supplied (feed) to the extracting agent (propane) was on average 6 wt. %. The empty-pipe speed of the extracting agent in the column was 2 mm/s.

The extracting agent conveyed out of the column head, loaded with oil, ethanol and some tocopherol, was evaporated in a separator at approximately 70° C. and 8 bar, and thus freed of the low-volatility oil, the tocopherol and most of the ethanol. The oil-free formulation formed (oil content less than 2 wt. %) was discharged at the bottom of the extraction column into an ambient-pressure environment by way of an arrangement of nozzles. Due to spontaneous evaporation of the propane, the formulation cooled and a free-flowing powder was obtained. The proportion of DL-α-tocopherol in the formulation was about 6 wt. %, which corresponds to a molar ratio of 0.1. The proportion of glycerol in the formulation was about 7 wt. %, which corresponds to a molar ratio of 0.6 (calculated on the basis of an average molecular weight of 700 daltons for the glycerophospholipids).

The formulation thus obtained showed excellent dispersibility and stability in water.

Example 5

Formulation of a Polar, Water-soluble Substance Using a Formulation Aid and One Solvent (triglycerides)

215 mg of the colouring agent Ponceau 4 R (E-124) were dissolved completely in 8 g of anhydrous glycerol at 50° C., added to 400 g of a mixture consisting of 65 wt. % glycerophospholipids (natural mixture from soybeans), and 35 wt. % triglycerides (soybean oil) and mixed carefully by stirring at 50° C. The mixture of dissolved substances was supplied by means of a high-pressure pump to an extraction column, approximately in the middle. The rectifying section of the column had about 5, and the stripping section about 7 theoretical stages. Compressed propane under a pressure of 60 bar served as extracting agent. At the feed stage of the column the temperature was about 75° C., at the top of the column 85° C. and at the bottom of the column 65° C. The ratio of the mixture supplied (feed) to the extracting agent (propane) was on average 5 wt. %. The empty-pipe speed of the extracting agent in the column was 2 mm/s.

The extracting agent conveyed out of the column head, loaded with oil, was evaporated in a separator at approximately 70° C. and 8 bar, and thus freed of the colourless oil. The oil-free formulation formed (oil content less than 2 wt. %) was discharged at the bottom of the extraction column into an ambient-pressure environment by way of an arrangement of nozzles. Due to spontaneous evaporation of the propane, the formulation cooled and a free-flowing red powder was obtained.

The proportion of colouring agent in the formulation was about 0.08 wt. %, which corresponds to a molar ratio of about 0.001, while the proportion of glycerol in the formulation was about 3 wt. %, which corresponds to a molar ratio of about 0.23, in each case expressed in terms of the glycerophospholipid (calculated on the basis of an average molecular weight of 700 daltons for the phospholipids).

The colouring agent formulation prepared in this way was stirred in a proportion of 2 %, at a temperature of 50° C., into refined soybean oil, producing a clear, red oil solution which was still stable after cooling to room temperature. In comparative experiments with non-formulated colouring agent and lecithin, there was no analogous colouring of the oil by the water-soluble colouring agent.

Example 6

Formulation of a Polar, Water-soluble Substance Without a Formulation Aid, Using Two Solvents (triglycerides and ethanol)

17.2 g glycolic acid were dissolved completely in 25 g ethanol (96 %) at room temperature, added to 300 g of a mixture consisting of 64 wt. % glycerophospholipids (natural mixture from soybeans) and 36 wt. % triglycerides (soybean oil), and mixed carefully by stirring at 45° C. The mixture of dissolved substances was supplied by means of a high-pressure pump to an extraction column, approximately in the middle. The rectifying section of the column had about 5, and the stripping section about 7 theoretical stages. Compressed propane under a pressure of 45 bar served as extracting agent. At the feed stage of the column the temperature was about 75° C., at the top of the column 85° C. and at the bottom of the column 65° C. The ratio of the mixture supplied (feed) to the extracting agent (propane) was on average 5 wt. %. The empty-pipe speed of the extracting agent in the column was 2 mm/s.

The extracting agent conveyed out of the column head, loaded with oil and ethanol, was evaporated in a separator at approximately 70° C. and 8 bar, and thus freed of the oil and the ethanol. The oil-free formulation formed (oil and ethanol content less than 2 wt. %) was discharged at the bottom of the extraction column into an ambient-pressure environment by way of an arrangement of nozzles. Due to spontaneous evaporation of the propane, the formulation cooled and a free-flowing powder was obtained.

The proportion of glycolic acid in the formulation was about 8 wt. %, which corresponds to a molar ratio of about 0.8, (calculated on the basis of an average molecular weight of 700 daltons for the phospholipids).

The glycolic acid formulation obtained in this way was dissolved in 50 % n-hexane by way of gentle heating. A clear, stable solution was obtained.

Example 7

Formulation of a Polar, Water-soluble Substance Using a Formulation Aid and Two Solvents (triglycerides and methanol)

6.5 g ascorbic acid were dissolved completely in a mixture of 19.1 g methanol and 5.8 g of anhydrous glycerol at 45° C., added to 300 g of a mixture consisting of 64 wt. % glycerophospholipids (natural mixture from soybeans) and 36 wt. % triglycerides (soybean oil), and mixed carefully by stirring at 60 CC. The mixture of dissolved substances was supplied by means of a high-pressure pump to an extraction column, approximately in the middle. The rectifying section of the column had about 5, and the stripping section about 7 theoretical stages. Compressed propane under a pressure of 50 bar served as extracting agent. At the feed stage of the column the temperature was about 75° C., at the top of the column 85° C. and at the bottom of the column 65° C. The ratio of the mixture supplied (feed) to the extracting agent (propane) was on average 5 wt. %. The empty-pipe speed of the extracting agent in the column was 2 mm/s.

The extracting agent conveyed out of the column head, loaded with oil and methanol, was evaporated in a separator at approximately 70° C. and 8 bar, and thus freed of the oil and the methanol. The oil-free formulation formed (oil and methanol content less than 2 wt. %) was discharged at the bottom of the extraction column into an ambient-pressure environment by way of an arrangement of nozzles. Due to spontaneous evaporation of the propane, the formulation cooled and a free-flowing powder was obtained. The proportion of ascorbic acid in the formulation was about 3.5 wt. % and the proportion of glycerol about 3 wt. %; this corresponds to a molar ratio of about 0.13 and 0.23 respectively (calculated on the basis of an average molecular weight of 700 daltons for the phospholipids).

The formulation was dissolved in a proportion of 1 % in lard, and subjected to an accelerated oxidation test at 110° C. in a so-called rancimat. Compared with the blank reading (formulated matrix of lecithin and glycerol without ascorbic acid), the formulation showed significantly improved oxidative stability.

Example 8

Formulation of a Polar Substance Using a Formulation Aid and Two Solvents (triglycerides and ethanol)

1.8 g ketoprofen were dissolved completely in a mixture of 10 g ethanol and 5 g anhydrous glycerol at 45° C., added to 156 g of a mixture consisting of 64 wt. % glycerophospholipids (natural mixture from soybeans) and 36 wt. % triglycerides (soybean oil), and mixed carefully by stirring at 60 C. The mixture of dissolved substances was supplied by means of a high-pressure pump to an extraction column, approximately in the middle. The rectifying section of the column had about 5, and the stripping section about 7 theoretical stages. Compressed propane under a pressure of 50 bar served as extracting agent. At the feed stage of the column the temperature was about 75° C., at the top of the column 85° C. and at the bottom of the column 65° C. The ratio of the mixture supplied (feed) to the extracting agent (propane) was on average 4 wt. %. The empty-pipe speed of the extracting agent in the column was 2 mm/s.

The extracting agent conveyed out of the column head, loaded with oil and ethanol, was evaporated in a separator at approximately 70° C. and 8 bar, and thus freed of the oil and the ethanol. The oil-free formulation formed (oil and ethanol content less than 2 wt. %) was discharged at the bottom of the extraction column into an ambient-pressure environment by way of an arrangement of nozzles. Due to spontaneous evaporation of the propane, the formulation cooled and a free-flowing powder was obtained. The proportion of ketoprofen in the formulation was about 11 wt. % and the proportion of glycerol about 5 wt. %; this corresponds to a molar ratio of about 0.32 and 0.38 respectively (calculated on the basis of an average molecular weight of 700 daltons for the phospholipids).

The powdery formulation showed excellent dispersibility in aqueous media.

Example 9

Formulation of a Polar Substance in Lyso-lecithin, Without a Formulation Aid, Using Two Solvents (triglycerides and ethanol)

10 g of salicylic acid were dissolved completely in 10 g ethanol at room temperature, added to 192 g of a mixture consisting of 64 wt. % enzymatically hydrolysed glycerophospholipids (Emulfluid E from the company Lucas Meyer, natural mixture from soybeans) and 36 wt. % triglycerides (soybean oil), and mixed carefully by stirring at 60° C. The mixture of dissolved substances was supplied by means of a high-pressure pump to an extraction column, approximately in the middle. The rectifying section of the column had about 5, and the stripping section about 7 theoretical stages. Compressed propane under a pressure of 70 bar served as extracting agent. At the feed stage of the column the temperature was about 75° C., at the top of the column 95 C and at the bottom of the column 55° C. The ratio of the mixture supplied (feed) to the extracting agent (propane) was on average 3 wt. %. The empty-pipe speed of the extracting agent in the column was 2 mm/s.

The extracting agent conveyed out of the column head, loaded with oil and ethanol, was evaporated in a separator at approximately 70° C. and 8 bar, and thus freed of the oil and the ethanol. The oil-free formulation formed (oil and ethanol content less than 2 wt. %) was discharged at the bottom of the extraction column into an ambient-pressure environment by way of an arrangement of nozzles. Due to spontaneous evaporation of the propane, the formulation cooled and a fine, free-flowing powder was obtained. The proportion of salicylic acid in the formulation was about 5 wt. %, which corresponds to a molar ratio of about 0.18 (calculated on the basis of an average molecular weight of 500 daltons for the hydrolysed phospholipids).

The powdery formulation showed excellent dispersibility in aqueous media.

What is claimed is:

1. A method of producing a homogeneous, anhydrous powder, the powder including as component as component (A) at least one glycerophospholipid; as component (B) at least one substance showing an affinity with glycerophospholipids selected from the group consisting of polar and lipophilic substances; wherein said component (A) and said component (B) are present in a molar ratio of 1:0.001 to 1:2; and optionally as component (C) a formulation aid comprising at least one anhydrous liquid $C_2$ to $C_4$ compound having at least two hydroxyl groups; wherein said component (A) and said component (C) are present in a molar ratio of from 1:0.001 to 1:1; said method consisting essentially of the steps of:

(a) dissolving component (B) in at least one liquid selected from the group consisting of 1) an anhydrous solvent and 2) component (C);

(b) dissolving glycerophospholipid component (A) in at least one solvent selected from the group consisting of an anhydrous solvent and an anhydrous solvent containing the formulation aid component (C);

(c) combining the liquids from steps (a) and (b), wherein the dissolved state of said components in the resulting solution is maintained, and (d) subjecting the solution from method step (c) to a fluid/fluid phase extraction process to remove the solvents and produce the anhydrous, homogeneous powder, wherein, if formulation aid (C) is present, glycerophospholipid (A) and said formulation aid (C) are present in said powder in a molar ratio of from 1:0.001 to 1:1.

2. The method of claim 1, wherein the extraction of the solution from step (c) is conducted in a rectifying column with an extracting agent containing at least one of propane and butane under a pressure between 1 and 50 MPa and a temperature from 20 to 150° C., wherein the extraction mixture separates into a homogeneous lower phase comprising glycerophospholipid component (A), component (B) and optionally component (C), and an upper phase containing the solvent and optionally component (B), wherein component (B) can be distributed from the upper phase to the lower phase due to its exceeding the solubility limit, the lower phase separating from the upper phase, and the formulation being obtained from the lower phase.

3. The method according to claim 1, wherein in at least one of steps (a) and (b) the solvent comprises at least one aliphatic or cyclic $C_{5-10}$ hydrocarbon.

4. The method of claim 3, wherein the solvent is selected from hexane, cyclohexane, and triglycerides.

5. The method according to claim 1, wherein in at least one of steps (a) and (b), the solvent comprises a polar protic or aprotic solvent.

6. The method of claim 5, wherein the protic solvent is selected from at least one of the group consisting of primary monovalent $C_{1-10}$ alcohols, secondary monovalent $C_{3-10}$ alcohols and monovalent $C_{4-10}$ alcohols.

7. The method of claim 5, wherein the aprotic solvent is at least one aprotic solvent selected from the group consisting of a halogenated $C_{1-10}$ hydrocarbon, ethers, and tetrahydrofuran.

8. The method according to claim 2, wherein in step (d), the extracting agent comprises up to 95 wt. % dimethyl ether.

9. The method according to claim 1, wherein the extraction in step (d) is carried out under a pressure between 3 and 20 MPa and at a temperature from 30 to 100° C.

10. The method according to claim 1, wherein the extraction is a continuous countercurrent process.

11. The method of claim 1, wherein a temperature gradient is set in the rectifying column such that the temperature at the top of the column is 5 to 50° C. higher than that at the bottom of the column.

12. The method of claim 2, wherein the lower phase containing the formulation is freed of extracting agent by at least one of reducing the pressure and by raising the temperature.

13. The method of claim 4, wherein the triglyceride is a natural vegetable oil.

14. The method of claim 1, wherein the solvent used of at least one of step (a) and step (b) is selected from the group consisting of chloroform and diethyl ether.

* * * * *